United States Patent [19]

Melrose et al.

[11] Patent Number: 5,290,894
[45] Date of Patent: Mar. 1, 1994

[54] BIOSTATIC AND BIOCIDAL COMPOSITIONS

[75] Inventors: Graham J. H. Melrose, Dalkeith; Concetta M. Kleppe, Bentley; Jeffrey W. Langley, Willetton; Jeffrey M. Stewart, Alfred Cove; Jacobus Van Dyk, Armadale, all of Australia

[73] Assignee: Biopolymers Limited, Australia

[21] Appl. No.: 381,404

[22] PCT Filed: Dec. 21, 1987

[86] PCT No.: PCT/AU87/00435
§ 371 Date: Jul. 31, 1989
§ 102(e) Date: Jul. 31, 1989

[87] PCT Pub. No.: WO88/04671
PCT Pub. Date: Jun. 30, 1988

[30] Foreign Application Priority Data

Dec. 23, 1986 [AU] Australia .................. PH9657

[51] Int. Cl.⁵ ............... C08F 16/34; A61K 31/765
[52] U.S. Cl. .................. 526/315; 424/78.08; 424/78.37
[58] Field of Search .......... 526/315; 424/78, 81, 424/78.08, 78.37; 523/175

[56] References Cited

U.S. PATENT DOCUMENTS

| | | | |
|---|---|---|---|
| 2,657,192 | 10/1953 | Miller et al. | 260/67 |
| 3,079,357 | 2/1963 | Fischer | 260/29.6 |
| 3,149,000 | 9/1964 | Beicos | 525/127 |
| 3,235,524 | 2/1966 | Kern et al. | 260/29.6 |
| 3,397,172 | 8/1968 | Schuler et al. | 526/315 |
| 3,635,898 | 1/1972 | Lorenz et al. | 260/67 |
| 3,843,684 | 10/1974 | Randall | 260/326.25 |
| 4,016,127 | 4/1977 | Larsen et al. | 260/29.6 |
| 4,479,820 | 10/1984 | Merk et al. | 504/161 |

FOREIGN PATENT DOCUMENTS

| | | | |
|---|---|---|---|
| 1255661 | 7/1963 | Australia . | |
| 0723213 | 12/1965 | Canada | 526/315 |
| 745398 | 12/1966 | Canada . | |
| 748848 | 12/1966 | Canada . | |
| 748859 | 12/1966 | Canada . | |
| 946663 | 1/1964 | United Kingdom . | |

OTHER PUBLICATIONS

M. Ishanov et al., "Radiation-Induced Crosslinking of Cellulose with Acrolein", *J. Polymer Science*, 9:1013–1025 (1971).

Kirk–Othmer, *Encyclopedia of Chemical Technology*, 1:284–286 (1978).

International Search Report from related International Application PCT/AU 87/00435.

*Encyclopedia of Polymer Science and Technology*, 2, Interscience Publishers, 1965, pp. 492–495 and 524–525.

*Kirk–Othmer Encyclopedia of Chemical Technology*, 13, Wiley–Interscience, New York, 1981, pp. 247–248.

*Primary Examiner*—Paul R. Michl
*Assistant Examiner*—Peter Szekely
*Attorney, Agent, or Firm*—Merchant, Gould, Smith, Edell, Welter & Schmidt

[57] ABSTRACT

Polymeric compounds having a polyacrolein sub unit in aldehyde, hydrated, hemi acetal or acetal form are provided which have biocidal or biostatic properties. The polymeric compound may be used to treat, or be included in, a wide range of products.

27 Claims, No Drawings

BIOSTATIC AND BIOCIDAL COMPOSITIONS

The present invention relates to new polymeric biocidal or biostatic compounds and to the treatment of substrates or substrate materials therewith and relates particularly but not exclusively to polymeric acrolein biocidal or biostatic compounds and to substrates or substrate materials treated therewith.

As is well known a biocidal substance kills microorganisms and a biostatic substance inhibits the growth of microorganisms; microorganisms including for example, bacteria, fungi and viruses. It is also known that aldehydes such as glutaraldehyde and formaldehyde are biocidal or biostatic and that substrates or substrate materials may be treated with such substances or compositions to render them at least temporarily biocidal or biostatic. The disadvantages of the use of such substances or such compositions is that the aldehydes have penetrating, obnoxious odours and are volatile thus rendering them unsuitable for long term biocidal or biostatic treatment of substrates or substrate materials.

As a result of microbial action, untreated substrates or substrate materials may be subject to deterioration or production of odours or formation of obnoxious or slippery slime or mildew or give rise to inflammation or transfer of disease. Thus, it is desirable that such substrates or substrate materials can be treated to render them biocidal or biostatic.

Another disadvantage of such conventional biostatic or biocidal compounds or compositions is that they are relatively low molecular weight and therefore pass relatively freely through biological membranes such as the skin or the intestinal wall and in both cases, into the blood stream of humans or animals where they may give rise to antigenic, allergenic or toxic effects; similar destructive or toxic results may arise from for example, passage through the roots or outer membranes of fruits or vegetables. Thus, there is a need for biostatic or biocidal compounds or compositions which do not readily pass through biological membranes.

Prior art such as French Patent 1312166, British Patent 946663 and U.S. Pat. Nos. 3,635,898 and 4,016,127, for example, disclose methods of polymerising acrolein for various purposes such as in the treatment of leather to provide improved mechanical properties. However no prior art recognises that such polymers or polymerization reactions provide biostatic or biocidal properties to substrates treated by such polymers or polymerization processes or that any polymers so produced have biostatic or biocidal properties.

Kirk-Othmer "Encyclopaedia of Chemical Technology" (Third Edition) volume 13—Wiley-Interscience (New York) and "Encyclopaedia of Polymer Science and Technology" Volume 2, 1965 Interscience Publishers (New York) similarly do not refer to any known biostatic or biocidal properties of acrolein polymers or substrates treated with such polymers. Kirk Othmer refers to the anti fungal or anti slime properties of acrolein monomer. However there is no suggestion that any acrolein polymer may have similar properties. Kirk Othmer also states that no commercial uses are known for acrolein polymers.

Further prior art—Journal of Polymer Science Vol 9, 1971, 1013-1025, Ishavov, Azizov, Negmankhodzhayeva and Usamov discloses treatment of cellulose with acrolein to improve mechanical properties of the cellulose. The authors conclude that "no acrolein homopolymer is formed in the vapour systems." and that the footnote to the relevant table 8 refers to the cross-linking having been done in the vapour phase. This excludes any conclusion that the antimicrobial property relates to polyacrolein polymer; the total context of the paper is of cross-linking in the absence of polyacrolein polymer, being due to monomeric joining of cellulose by the double bond and the carbonyl group, respectively of acrolein monomer.

It has now been discovered that polymeric compounds having, illustratively, the repeating unit

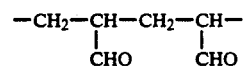

may be utilized as biocidal or biostatic compounds and for the treatment of substrates or substrate materials to render them biocidal or biostatic. However, it is stressed that such polymeric compounds having this repeating unit do not exist at equilibrium, entirely in these illustrated open chain forms in which the aldehyde groups are entirely un-associated. Specifically, we have discovered that polymers or copolymers of acrolein or of an aldehyde-derivative of acrolein may be utilised as biostatic or biocidal compounds and for the treatment of substrates or substrate materials to render them biostatic or biocidal.

The invention lies in the recognition of the similarities in structure between glutaraldehyde, which is a known bacteriostat and bacteriocide, and polymers or copolymers of acrolein or of an aldehyde-derivative of acrolein. In the case of polyacrolein, for example, at equilibrium the structure takes on a number of different forms; it is generally agreed (E. Bergman, W. T. Tsatsos and R. F. Fischer, J. Polymer Sci: Part A, 1965, 3485; R. C. Schulz, Vinyl Polym., 1967, 1, 403; L. Hunter and J. W. Forbes, J. Polymer Sci: Part A, 1965, 3, 3471 that subunits of polyacrolein produced by a free radical inducing agent have the structures below ((a); R=H):

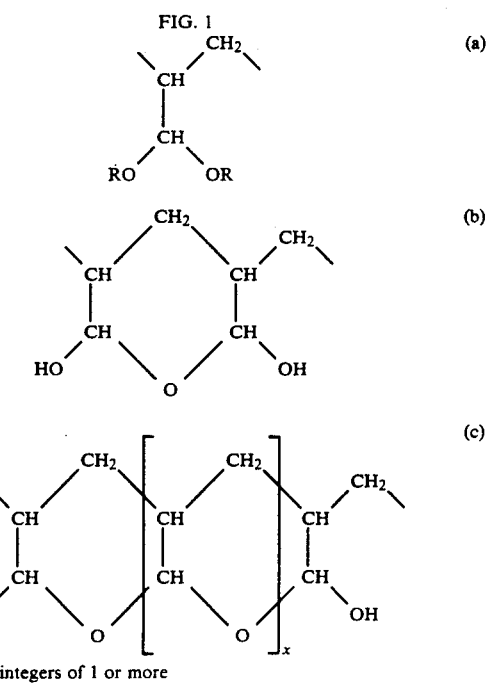

FIG. 1 x = integers of 1 or more

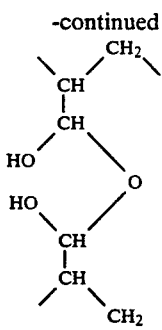
(d)

in which either the form (d) or the tetrahydropyran ring-form (b) or the fused tetrahydropyran ring-form (c) predominate. $^{13}$C—NMR analysis of polyacrolein produced by a free radical inducing agent (free radical catalyst) showed negligible aldehyde carbon, which is consistent with the above structures; the spectrum also showed a number of aliphatic CH's and CH$_2$'s and a number of O—CH—O's which are all expected from the above variety of structures.

In keeping with proposals of R. C. Schulz, Vinyl Polym., 1967, 1, 403, the $^{13}$C—NMR spectrum of polyacrolein produced by an ionic catalyst is consistent with the above structures for the polymer and additionally, the presence of structures (a) and (b) of FIG. 2.

FIG. 2

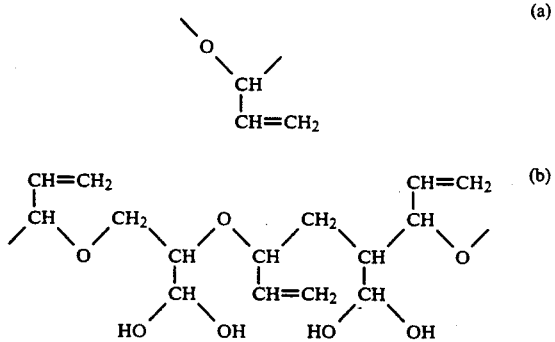

(a)

(b)

The $^{13}$C—NMR spectrum of a copolymer of acrolein diethylacetal: acrylic acid was consistant with the polymer having repeating units illustrated by FIG. 1 (a); R=CH$_3$CH$_2$.

Glutaraldehyde is proposed to exist in the following forms (A. D. Russell and D. Hopwood, "Progress in Medicinal Chemistry", Vol. 13, Eds. G. P. Ellis and G. B. West, North Holland Publishing Company, 1976):

FIG. 3

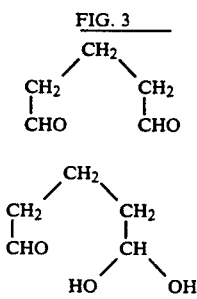

(a)

(b)

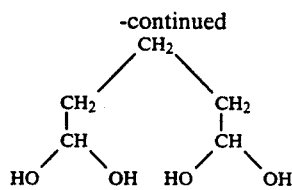
(c)

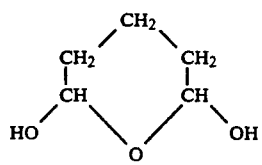
(d)

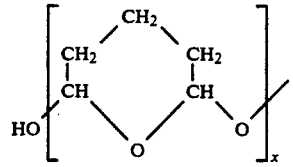
(e)

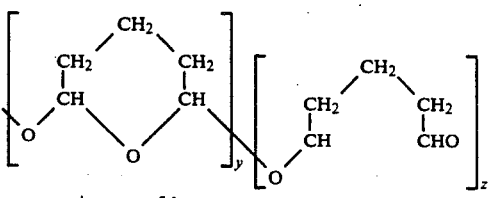
(f)

x, y, z = integers of 1 or more

The $^{13}$C—NMR analysis of glutaraldehyde showed that very little of the glutaraldehyde (less than 5%) existed in the free aldehyde form (a). There were many aliphatic CH$_2$ resonances evident in the spectrum with the major peaks numbering eleven. There were also many O—CH—O resonances with nine major peaks. This supports the existence of the above cyclic structures as the linear forms of glutaraldehyde would not give rise to so many different resonances.

According to our invention, an added advantage of these polymers or copolymers of acrolein or of an aldehyde-derivative of acrolein is that their hydrophilicity/hydrophobicity or water solubility/oil or lipid solubility may be widely adjusted by the inclusion or exclusion, respectively, of hydrophilic comonomers, for example, acrylic acid, vinyl pyrrolidone, vinyl or acrylic monomers containing oxygen-containing groups for example, hydroxyl groups, or ether groups or carboxyl groups, or other similar hydrophilic monomers which will now be apparent to those skilled in the art. Normally, the homopolymers of acrolein are water-insoluble and are thus suited to applications where their elution by aqueous media are not desirable as in sprays for agricultural or veterinary purposes or in applications where the utility of the polyacrolein is sought in oil phases such as some cosmetic/toiletry preparations or foods or engine oils; alternatively, the inclusion of a high percentage of hydrophilic comonomer for example, acrylic acid renders the resulting copolymer suited to use in hydrophilic media which is more usual in cosmetics, toiletries, pharmaceuticals or food substances. Water-dispersable or water-soluble copolymers of acrolein, for example, the 90:10 acrylic acid: acrolein copolymer is especially suited as a sterilent, sanitiser, antimicrobial or preservative in cosmetics, toiletries, pharmaceuticals or food substances. A particular application which we record is that we project copolymers of acrolein or of a carbonyl-derivative of acrolein may be dissolved in an aqueous solution or in a gel-like medium formed through, for example, the presence of carboxymethylcellulose and then the resulting solution or gel used as a rectal suppository to combat the transmission of AIDS virus amongst homosexuals. Also the solution or gel could be enclosed in a small tube (as toothpaste is conventionally dispensed)—the cap of the tube incorporating a syringe-needle which is made available to drug addicts who are in danger of transmitting AIDS through unclean injection-techniques; of course, the storing of the syringe-needle in the solution or gel would have a biostatic or biocidal effect against the aids microorganism.

A further advantage of the said polymers or copolymers of acrolein or of a derivative of acrolein is that their biostatic or biocidal activities appear to be less pH-dependent than glutaraldehyde (see S. D. Rubbs et at., J. Appl. Bact., 1967, 30(1), 78).

An advantage of using an aldehyde-derivative of acrolein is absence or greatly reduced acrid smell, compared with acrolein, during the polymerization. Of course, however, all final polymers and even those prepared from acrolein are essentially odour-free.

Substrates which can be treated with the compounds of the invention include cellulose, modified cellulose, regenerated cellulose, rayon, natural or synthetic polymers of thermo-setting or thermo-plastic materials, natural or synthetic fibres or resins including such as vinyl polymers, acrylic polymers, polyamides, polyesters, rubbers and various materials such as surface coatings, ceramics, glass, concrete, wood, masonry, metals, minerals and earths.

Examples of substrate materials which may be made by such substrates are:

Air conditioner filters, air-line wipes, aprons, bags for laundry, bandages or adhesive bandages, bathroom tiles or grout, bricks, car or other carpets, catheters and related hospital instruments made from plastic or glass, clothing including underwear, cloth wraps for food, concrete, cotton-balls or cotton tips (buds), diapers, disposable towels, drapes (domestic, commercial, industrial or hospital), disposable cardboard or plastic food boxes, face masks (hospital or industrial) bed covers, inners of shoes, ironing board covers, jumpers or cardigans, nursing pads, paint for ships' hulls or underwater pylons, paper plates and cups, water reservoirs or swimming pools or water-treatment chemicals, rubbish bins made from cardboard or plastic, sanitary napkins or feminine hygiene tampons, sheeting for babies' or incontinent persons' beds, shelving paper, shower curtains, socks, sterile gloves, sterile overalls, teatowels, telephones—diaphragms for mouth pieces, tents, tissues, handkerchiefs, toilet paper, toothbrush nylons, towels, wall paper, window awnings or other like structures made from canvas plastic etc., wipes, mops, sponges, wood or wood-impregnants.

It has now also been discovered that polymerization of acrolein or an aldehyde-derivative of acrolein, with or without other comonomer in the presence of a substrate or substrate material causes the polymer to chemically bond to the substrate such as through graft polymerization. This has the advantage that the biocidal or biostatic agent is not readily removed from the substrate. Thus, the effect of the biocidal or biostatic agent may be longer-lasting than in cases where there is no chemical bond.

The rendering of the substrate biocidal or biostatic either prevents microbiological degradation of the substrate, prevents the production of odours which may result from degradation of the substrate or from the degradation of chemical compounds contained in or within the substrate. This rendering also prevents the substrate from being a vector of inflammation or disease. Further, mould, lichen or other similar formation on the substrate may be prevented. The biostatic or biocidal agent of the present invention may be associated with materials from which substrates are made, so as to be incorporated into the final product or alternatively, the finally fabricated substrate may be suitably treated to associate it with the biocidal or biostatic agent.

The present invention therefore provides a polymeric biocidal or biostatic compound having the polymeric repeating unit or this repeating unit in hydrated, hemi-acetal or acetal forms described earlier (FIGS. 1 and 2), such biostatic or biocidal compound having the repeating unit(s) being derived from a polymer or copolymer of acrolein or of an aldehyde-derivative of acrolein.

The invention also provides a composition of matter comprising a polymeric biocidal or biostatic compound having the polymeric repeating unit or this repeating unit in hydrated, hemi-acetal or acetal forms described earlier (FIGS. 1 and 2), such biostatic or biocidal compound having the repeating units(s) being derived from a polymer or copolymer of acrolein or of an aldehyde-derivative of acrolein bound to a substrate or substrate material.

The invention also provides a process for preparing a polymeric biocidal or biostatic compound having the polymeric repeating unit or this repeating unit in hydrated, hemi-acetal or acetal forms described earlier (FIGS. 1 and 2), such biostatic or biocidal compound having the repeating unit(s) being derived from a polymer or copolymer of acrolein or of an aldehyde-derivative of acrolein such polymerisation taking place in the presence of a polymerisation-inducing agent; the agent is either a free-radical initiator, or an ionic initiator. The compounds or compositions of the invention may be as a antimicrobial or preservative for water, water-containing compositions, food, cosmetics, toiletries, pharmaceuticals, or oils or lubricants; as an intimocrobial, sterilent, antimicrobial, antiseptic, disinfectant or sanitiser in industrial, agricultural, veterinary or human health-care applications; or as a solid liquid, solution, emulsion, suspension or gel, including such applications as for specific use against viruses and such related microorganisms in the form of a solid, liquid, solution, gel, emulsion or suspension of matter.

The invention also provides a method of producing a composition of matter which comprises polymerizing acrolein or a derivative thereof in the presence of or with a substrate or substrate material preferably in the presence of a polymerization inducing agent. The polymerization inducing agent is preferably selected from gamma radiation, such as is produced by a radioactive cobalt source. The present invention also relates to methods of rendering substances or compositions biocidal or biostatic and to uses of such biocidal or biostatic substances or compositions. The invention also relates to the uses of polymeric compounds as herein described to render substances or compositions biocidal or biostatic.

The invention will now be illustrated by the following non-limitative examples.

EXAMPLE 1

Preparations and Structures of Polyacrolein (a) Using a free radical inducing agent (free radical catalyst): 9.64 g distilled acrolein and 25 g methanol were placed in a 100 ml round bottom flask and purged with nitrogen. 0.525 g benzoyl peroxide was added and the solution stirred under nitrogen at 60 degrees centigrade. The reaction was allowed to continue for a total of ca. 88 hours. After this time the reaction solution had become strongly yellow in colour and had a solids content of 30.5%.

$^{13}$C—NMR (300 MHZ)δ(relative to d$_4$-methanol at 49.00): 33.27 (CH); 33.53 (CH); 33.79 (CH); 33.87 (CH$_2$); 37.03 (CH); 37.29 (CH); 37.54 (CH); 37.64 (CH$_2$); 97.15 (CH); 103.37 (CH); 104.34 (CH); 139.36 (CH); 139.78 (CH$_2$); 196.72 (CH). The $^{13}$C—NMR spectrum shows some residual acrolein with the aldehyde carbon at δ196.72 and the vinylic CH$_2$ and CH at δ139.78 and δ139.36, respectively; apart from the δ196.72 (CH) resonance absorption, there was no other attributed to —CHO. The spectrum is consistent with polymeric acrolein consisting of fused tetrahydropyran rings and some free dihydroxy methyl groups. The rings exist in either the boat or chair configurations giving rise to more chemical shifts than may be expected.

A similar polymerization of acrolein was also carried out: 25.02 g methanol was placed in a reaction vessel fitted with a thermometer, reflux condenser and nitrogen inlet tube. 0.528 g of benzoyl peroxide was added and 9.65 g of distilled acrolein was added. The system was purged with nitrogen and heated in an oil bath at 60 degrees centigrade with stirring, for 24 hours; when a solids determination indicated 20% conversion; total conversion was 40% after a further 48 hours heating.

Typically, as an indication of molecular weight, the polyacrolein was found to have a retention time which was shorter than that of polyethyleneglycol 10,000 on a Porasil GPC 60 Angstrom column using a Waters Associated Model ALC/GPC 204 liquid chromatograph fitted with a differential refractometer R401.

(b) Using an ionic catalyst: 1.6 g distilled acrolein was made up to 20 ml with deionised water in a 200 ml beaker and then, ca. 0.5 ml of 0.2M sodium hydroxide added with stirring to pH ca. 10–11. The solution became cloudy and a white precipitate began to form. The contents were stirred for a further 2 hours and then filtered. The precipitate was washed thoroughly with deionised water until the filtrate was neutral. The product was dried under vacuum and was a white-pale yellow, fine powder; it readily dissolved in methanol—and conveniently and importantly, could be evaporated down to dryness and then again, dissolved in methanol or other solvents. In a similar determination to the above, the polyacrolein was found to have a retention time which was shorter than that of polyethylene glycol 10,000. $^{13}$C—NMR (300 MHz) δ(relative to d$_4$-methanol at 49.00): 19–31 (CH$_2$); 35.95 (CH$_2$); 37–42 (CH); 62–73 (CH$_2$) 73–81 (CH); 92–95 (CH); 96–103 (CH); 114–120 (CH$_2$); 134–141 (CH); 196.0 (CH).

EXAMPLE 2

Preparation of 90:10 Acrylic Acid: Acrolein Copolymer 6.489 g distilled acrylic acid, 0.56 g distilled acrolein and 15 g methanol were placed in a 50 ml round bottom flask and purged with nitrogen. 0.33 g benzoyl peroxide was added and the solution stirred under nitrogen at 60–65 degrees centigrade. The reaction was continued for ca. 66 hours. After this time the contents of the flask had become very viscous, having a solids content of 57.7% (indicating 100% conversion).

A sample of the viscous material was placed on a petri dish and dried on a hot plate to remove solvent. Drying was completed in an oven at 80 degrees centigrade and a transparent, slightly yellow coloured polymer was obtained. The copolymer is completely soluble in warm water (ca. 50 degrees centigrade) and once dissolved remains so, even on cooling the solution.

In order to ensure that the solids obtained were polymeric, a simple dialysis experiment was performed: 10 g of an aqueous solution containing 0.65% solids was placed in a dialysis tube. This was irrigated with water continuously for ca. 66 hours. The solution in the dialysis tube was then recovered and the solids content determined at 0.68%. Since the solids were completely retained and the lower limit for solids penetration through the dialysis tube is 2000 m wt, we conclude that the solids are polymeric.

EXAMPLE 3

2.8 g of acrolein diethyl acetal was placed in a 100 ml round bottom flask and the contents purged with nitrogen. A solution of 0.216 g potassium persulphate in 7.5 g water was added with stirring, under nitrogen. The flask was placed in an oil bath at 60–70 degrees centigrade and stirred for ca. 20 hours. A yellow solid was recovered and dried at 50 degrees centigrade; weight 0.915 g.

EXAMPLE 4

4 g distilled acrylic acid, 4.81 g acrolein diethyl acetal and 15 g methanol were placed in a 50 ml round bottom flask and purged with nitrogen. Then 0.3 g benzoyl peroxide was added and stirring continued under nitrogen at 60–65 degrees centigrade for 70 hours (solids determination indicated a 50% conversion). $^{13}$C—NMR (300 MHz) δ(relative to d$_4$-methanol at 49.00): 15.58 (CH$_3$); 18.31 (CH$_3$); 35.52 (CH$_2$); 36.24 (CH$_2$); 37.07 (CH$_2$); 42.36 (CH); 42.85 (CH); 58.32 (CH$_2$); 130.00 (CH); 131.57 (CH$_2$); 178.51 (CH).

EXAMPLE 5

3.8 g of acrolein diethyl acetal, 3.3 g vinyl pyrrolidone and 10 g methanol were placed in 50 ml round bottom flask and thoroughly purged with nitrogen. 0.71 g azobisisobutyronitrile was added and the flask heated in an oil bath at 60-65 degrees centigrade, with stirring under nitrogen for 72 hours when the conversion was 44%. The copolymer was found to be soluble in methanol.

EXAMPLE 6

In a similar technique to the above, 3.9 g acrolein diethyl acetal, 1.16 g acrylic acid, 7.5 ml water and 0.216 g potassium persulphate were heated under nitrogen, with stirring in an oil bath at 60-70 degrees centigrade for ca. 24 hours when a white waxy material was recovered; it was insoluble in water, but swelled in methanol, acetone, tetrahydrofaran or methyl ethyl ketone.

EXAMPLE 7

A similar result was achieved through heating and stirring in the usual way to the above: 14.5 g methanol, 3.62 g distilled acrolein, 1.21 g distilled acrylic acid and 0.265 g benzoyl peroxide. After 40 hours the conversion was 40%.

EXAMPLES 8-11

A 50:50 mixture of monomers was treated as follows: 2.35 g distilled acrolein, 2.88 g distilled acrylic acid and 14.5 g methanol were placed in a 50 ml round bottom flask and flushed with nitrogen. 0.2625 g benzoyl peroxide was added and after heating at 60-70 degrees centigrade for 48 hours the conversion was 70%. The polymer swelled in methanol but was insoluble in water.

Similar preparations were achieved with different ratios of the monomers acrolein: acrylic acid namely, 30:70 (Example 9), 10:90 (Example 10), 2.5:97.5 (Example 11). The products from Examples 10 and 11 were soluble in water and retained by dialysis tubing of exclusion 2,000 mwt.

EXAMPLE 12

In a similar preparation to the above, 42% conversion was achieved of a polymer which swelled in methanol or water, from 1.8 g acrolein, 3.3 g vinyl pyrrolidone and 0.071 g azobisisobutyronitrile.

EXAMPLE 13

30 mg benzoyl peroxide was added to a solution of 1.02 g polyethyleneglycol acrylate and 0.5 ml acrolein in 5 ml methanol. The mixture was stirred and heated to reflux for 48 hours and gave 90% conversion; the residual oil (1.2 g) was chromatographed on Sephadex LH-20 (18 g) in methanol. The structure of the resulting polymer was confirmed by NMR analysis.

EXAMPLES 14-19

Whatman 5.5 cm filter paper was immersed in the following solutions and irradiated by a cobalt source for 4 hours:

| Example | Acetyl diethyl acetal | Acrylic Acid | Methanol |
|---|---|---|---|
| 14 | 2.0 ml | 0 ml | 18 ml |
| 15 | 1.6 ml | 0.4 ml | 18 ml |
| 16 | 1.2 ml | 0.8 ml | 18 ml |
| 17 | 1.0 ml | 1.0 ml | 18 ml |
| 18 | 0.4 ml | 1.6 ml | 18 ml |
| 19 | 2.0 ml* | 0 ml | 18 ml |

*Acrolein diacetoxy acetal

Filter papers were dried in an oven at 70 degrees centigrade for 30 minutes and weighing indicated the grafting of polymer 0.8%-12.6%. (These yields were recorded after washing with methanol).

EXAMPLE 20

A small cellulosic paper disk which is normally used for filtration i.e. a filter paper, about 2 cms. in diameter was immersed in a 10% solution of acrolein in water (10 ml), contained in a tube. The tube and its contents were flushed with nitrogen, sealed, and then gamma-radiated for one hour from a cobalt source (approximately 0.7 Mrad/hour). The disk was then removed and washed with water.

The following standard strains were used for testing:
a) *Staphylococcus aureus* (Oxford)
b) Pseudomonas ATCC
c) Candida ATCC Dilutions were prepared in normal saline.

10 ul of each bacterial solution was applied to 1 square centimeter of test filter paper. Filter papers were maintained in a moist atmosphere at room temperature for 2 hours. Filter papers were then transferred to 5 ml heart brain infusion and shaken at 37 degrees centigrade for 30 minutes. 10 ul was removed for sterility testing and the flasks incubated at 37 degrees centigrade for 18 hours. The flasks were inspected for growth and the growth was checked on blood agar.

| Concentration cfu/ml (10 log) | Staphylococcus | | Pseudomonas | | Candida | |
|---|---|---|---|---|---|---|
| | Control | Test | Control | Test | Control | Test |
| 10 | + | − | + | − | | |
| 9 | + | − | + | − | + | − |
| 8 | + | − | − | − | + | − |
| 7 | + | − | − | − | + | − |
| 6 | + | − | − | − | + | − |
| 5 | + | − | − | − | + | − |
| 4 | + | − | − | − | + | − |
| 3 | + | − | − | − | − | − |

+ = growth
− = kill

EXAMPLE 21

Whatman No. 4 filterpaper was impregnated with a solution of polyacrolein in methanol which had been polymerised by means of gamma-radiation) and dried in an oven at 70 degrees centigrade for 1 hour. The amount of impregnated polymeric antimicrobial was 9%. The impregnated filter paper was tested for antimicrobial activity and the results were recorded by comparing with a control filter-paper.

The following standard strains were used for testing:
a) *Staphylococcus aureus* (Oxford)
b) Pseudomonas ATCC
c) Candida ATCC Dilutions were prepared in normal saline.

10 ul of each bacterial dilution was applied to 1 square centimeter of test filter paper. The filter papers were maintained in a moist atmosphere at room temperature for 2 hours. Then the filter papers were transferred to 5 ml heart brain infusion and shaken at 37 degrees centigrade for 30 minutes. 10 ul was removed for sterility testing and the flasks incubated at 37 degrees centigrade for 18 hours. The flasks were inspected for growth and the growth was checked on blood agar.

| Concentration cfu/ml (10 log) | Staphylococcus Control | Staphylococcus Test | Pseudomonas Control | Pseudomonas Test | Candida Control | Candida Test |
|---|---|---|---|---|---|---|
| 10 | + | − | + | − |   |   |
| 9 | + | − | + | − | + | C |
| 8 | + | − | − | − | + | C |
| 7 | + | − | − | − | + | − |
| 6 | + | − | − | − | + | − |
| 5 | + | − | − | − | + | − |
| 4 | + | − | − | − | + | − |
| 3 | + | − | − | − | − | − |

+ = growth
− = kill
C = contaminated

EXAMPLE 22

Whatman No. 4 filterpaper was impregnated with a solution of polyacrolein. In methanol, which has been prepared by polymerising 19.3 g distilled acrolein in 58 g methanol in the presence of 1.05 g benzoylperoxide in a nitrogen atmosphere for 3 days at 70 degrees centigrade. The amount of impregnated polymeric antimicrobial was 8%. The impregnated filterpaper was tested for antimicrobial activity and the results were recorded by comparing with a control filterpaper.

The following standard strains were used for testing:
a) *Staphylococcus aureus* (oxford)
b) Pseudomonas ATCC
c) Candida ATCC Dilutions were prepared in normal saline.

10 ml of each bacterial dilution was applied to 1 square centimeter test filter paper. The filter papers were maintained in a moist atmosphere at room temperature for 2 hours. Then, the filter papers were transferred to 5 ml heart brain infusion and shaken at 37 degrees centigrade for 30 minutes. The flasks were incubated at 37 degrees centigrade for 18 hours, inspected for growth and the growth was checked on blood agar.

| Concentration cfu/ml (10 log) | Staphylococcus Control | Staphylococcus Test | Pseudomonas Control | Pseudomonas Test | Candida Control | Candida Test |
|---|---|---|---|---|---|---|
| 10 | + | − | + | − |   |   |
| 9 | + | − | + | − | + | − |
| 8 | + | − | − | − | + | − |
| 7 | + | − | − | − | + | − |
| 6 |   |   |   |   | C | − |

+ = growth
− = kill
C = contaminated

EXAMPLE 23

Twice, in separate experiments, cotton wool was impregnated with a solution of polyacrolein in methanol which had been prepared by polymerizing 19.3 g distilled acrolein in 58 g methanol in the presence of 1.05 g benzoylperoxide in a nitrogen atmosphere for 3 days at 70 degrees centigrade. The amount of impregnated, polymeric antimicrobial was 5% and 3.5% respectively. The impregnated cottonwools were tested for antimicrobial activity and the results were recorded by comparing with control cottonwool.

The following standard strains were used for testing:
a) *Staphylococcus Aureus* (Oxford)
b) Pseudomonas ATCC Dilutions were prepared in normal saline.

5 mg amounts of cottonwool were weighed and placed in sterile bijoux bottles. The cottonwool was saturated with 30 ul of 5 different bacterial dilutions. After 2 hours at room temperature, the cottonwool was transferred to 5 ml of heart brain infusion and incubated for 18 hours at 37 degrees centigrade. Cultures were inspected for growth and growth was checked by plating on blood agar.

| Concentration cfu/ml (10 log) | Staphylococcus Control | Staphylococcus 3.5% | Staphylococcus 5% | Pseudomonas Control | Pseudomonas 3.5% | Pseudomonas 5% |
|---|---|---|---|---|---|---|
| 5 | + | − | − | + | − | − |
| 4 | + | − | − | + | − | − |
| 3 | + | − | − | + | − | − |
| 2 | + | − | − | + | − | − |
| 1 | + | − | − | − | − | − |

+ = growth
− = kill

It will be evident that these laboratory scale examples may be extended to industrial scale processes, for example, in which the substrate cellulose, prior to incorporation in, for example, tampons, diapers or medical cellulosic products is treated with acrolein vapour or acrolein solution and is then gamma-irradiated. Further, the process may be extended to the continuous (as well as batch) industrial processes in which cotton, cellulosic fibre or other fibres are treated with acrolein vapours or solution prior to weaving or making into a non-woven fabric. Still further, the laboratory scale example may be extended to treating sheets, fabrics or cloths prior to making into clothes, drapes and other similar finished products. Still further, the example may be extended to treating the starting-materials or their final products such as ceramics, masonry, bricks, concrete, glass or plastics materials either prior to or after making these into their final fabricated forms.

EXAMPLE 24

Many other substrates were treated with solutions containing active polymers, for example, gauze from bandages, non-woven fabric from sanitary napkins, cottonwool from tampons—and always before microbiological testing, a control was used on the substrate which had been treated with the pure solvent (methanol). Substrates which had been treated with the methanolic solutions of the polymers were always dried at 80 degrees centigrade/1.5 hours before antimicrobial testing—and as well, extracts were made with both methanol and physiological saline to test for the presence of monomer; this was found by HPLC and GC to be less than 10 ppm at which the acrolein was found to be microbiologically inactive during our tests:

Cotton (3.876 g) with a 3% content of polyacrolein was agitated in saline (75 ml) for 24 hours.

The saline extract was analysed by GLC (10% carbowax 20M and FID detector) which showed that the cotton contained less than 20 ppm (the limit of detection).

The saline extract (50 ml) was added to a solution of 2,4-dinitrophenylhydrazine (0.100 g) in 2N hydrochloric acid (25 ml). The resultant solution was extracted with chloroform (3×5 ml). The combined organic fractions were then washed with 2N hydrochloric acid (2×5 ml), water (2×5 ml) and dried (sodium sulphate). The chloroform was evaporated to dryness and the residue dissolved in acetonitrile (1 ml). Analysis of the acetonitrile by HPLC (C18 reverse phase, 70% aqueous mmethanol, UV detector at 245 nm) showed that the cotton contained 2.4 ppm of acrolein.

Typically, substrates which were found to be microbiologically active, retained their activities after more than 6 months' standing at room temperature.

The following are typical and additional test-results, executed similarly to examples 20–23:

| Example No. | Active Agent | | |
|---|---|---|---|
| | Staphyloccocus | Pseudomonas | Candida |
| 1* | + | + | + |
| 2** | + | + | + |
| 3 | + | NT | NT |
| 4 | + | NT | NT |
| 5 | + | NT | NT |
| 6 | + | NT | NT |
| 7 | + | + | + |
| 8 | + | + | + |
| 9 | + | + | + |
| 10** | + | + | + |
| 11** | + | + | + |
| 12 | + | NT | NT |
| 13 | NT | + | NT |
| 14 | + | NT | NT |
| 15 | + | NT | NT |
| 16 | + | NT | NT |
| 17 | + | NT | NT |
| 18 | + | NT | NT |
| 19 | + | NT | NT |

NT = note tested
+ = positive/active
*(a) Tests were also carried out in phosphate buffers, adjusted with sodium hydroxide to give pH's of 5, 6, 7, 8 and 9, respectively; results against Staphlococcus (Oxford) at levels $10^3$–$10^8$ showed no differences in activities at the respective pH's. Activities were also retained at the level of 25 $\mu$l heparinized blood or urine, respectively (both human).
(b) In another experiment, a methanolic solution was applied to spore strips of Bacillus subtilis var niger and left in contact at room temperature for 2 hours before transferring to heart brain infusion for 18 hours/37 degrees centigrade. The cultures were inspected for growth and plated to blood agar - the solution of polymer being active against the spores, whilst the methanol-solvent was inactive under these conditions.
(c) In separate experiments, 0.1 g of cotton wool which had been coated with the polymer, was aseptically weighed into separate sterile bijoux bottles. The cotton wool was then incubated with 0.5 ml of dilutions of cultures of Erwinia carotovora (Important in soft rot of potatoes or cabbages), S. Aureus (important regarding bovine mastilis) and Salmonella dublin (important regarding bovine calf mortality), respectively. These were left at room temperature for 2 hours and then the cotton wool was transferred to TSB, an enriched nutrient broth and incubated at 32 degrees centigrade, 37 degrees centigrade and 37 degrees centigrade, respectively. The coating on the respective cotton wools killed the 3 organisms respectively, in the range $10^5$–10/ml of pathogen.
(d) In separate and similar experiments (except the media used was malt extract broth, Sabouraud dextrose agar, 0.1% peptone water as diluent), kills were achieved in the range $10^2$–$10^5$/ml of Aureobasidium pullurans (associated with black-slime on bathroom tiles and groutings) and Pycnoporus coccineus (associated with rotting in timbers).
(e) In 3 separate experiments, tests were also conducted for anti-viral activities and found active in each case, using the following method for Herpes Simplex, Enterovirus, Echo 11 and Influenza PR8, respectively: a $10^4$/ml suspension of the viral particles was applied to cottonwool treated with the antimocrobial polymer, followed by centrifugation. 0.1 ml aliquots of the centrifugate were introduced into cultures of human embryonic fibroblasts or HeLa cells and the cytopathic effect noted.
**Also active in a preservative test conducted over 14 days at pH 7.5 in glycerol-triethanolamine buffer, against Pseudomonas ATCC dilutions prepared in normal saline.

"Staphylococcus", Pseudomonas" and "Candida" referred to herein are more specifically identified as:
Staphylcoccus aureus NCTC 6571
Pseudomonas aeruginosa ATCC 27853
Candida albicans PMH 82/312

We claim:

1. A biocidal or biostatic article comprising a substrate to which is chemically bound, a biocidally or biostatically effective amount of a polymer or copolymer having the repeating polymeric unit

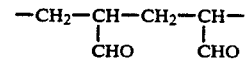

or the hydrated diol form thereof, the hemiacetal or acetal form thereof from condensation of the diol form with the aldehyde form, the tetrahydropyran or fused tetrahydropyran form thereof from self-condensation of the diol form, the aldol-Michael self-condensation form thereof or mixtures thereof, the article of manufacture being capable of killing or inhibiting the growth of microbes that contaminate the article.

2. A article of manufacture as claimed in claim 1, wherein the substrate is selected from the group consisting of cellulose, modified cellulose, regenerated cellulose, rayon, polymers of plastic materials, rubbers, ceramics, glass, silica, concrete, masonry, minerals and earths.

3. An article of manufacture as claimed in claim 2, wherein the polymers of plastic materials are vinyl polymers, acrylic polymers, polyamides, or polyesters.

4. A process for preparing an article of manufacture as claimed in claim 1, which comprises polymerizing acrolein or a (co)polymer or derivative thereof in the presence of the substrate or substrate material.

5. A process as claimed in claim 4, wherein the process is carried out in the presence of a polymerization inducing agent comprising an ionic catalyst, gamma radiation, a free radical catalyst, ultraviolet radiation or electron beam radiation or a combination thereof.

6. A process as claimed in claim 4, wherein the substrate is selected from the group consisting of cellulose, modified cellulose regenerated cellulose, rayon, polymers of plastic materials, rubbers, ceramics, glass, silica, concrete, masonry, minerals and earths.

7. A process as claimed in claim 5, wherein the substrate is selected from the group consisting of cellulose, modified cellulose regenerated cellulose, rayon, polymers of plastic materials, rubbers, ceramics, glass, silica, concrete, masonry, minerals and earths.

8. A process as claimed in claim 6, wherein the polymers of plastic material are vinyl polymers, acrylic polymers, polyamides, or polyesters.

9. A process as claimed in claim 7, where the polymers of plastic material are vinyl polymers, acrylic polymers, polyamides, or polyesters.

10. A process for rendering a substrate biocidal or biostatic, which comprises applying to the substrate a biocidally or biostatically effective amount of a polymer or copolymer having the repeating polymeric unit

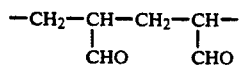

or the hydrated diol form thereof, the hemiacetal or acetal form thereof from condensation of the diol form with the aldehyde form, the tetrahydropyran or fused tetrahydropyran form thereof from self-condensation of the diol form, the aldol-Michael self-condensation form thereof or mixtures thereof.

11. A process as claimed in claim 10, wherein the composition containing said polymeric compound is in the form of a solid, liquid, solution, gel, emulsion or suspension.

12. A process as claimed in claim 10, wherein the matter is water, water-containing compositions, food cosmetics, toiletries, pharmaceuticals, oil or lubricants, cellulose, modified cellulose, regenerated cellulose, rayon, polymers of plastic materials, rubbers, ceramics, glass, silica, concrete, masonry or minerals.

13. A process as claimed in claim 11, wherein the matter is water, water-containing compositions, food, cosmetics, toiletries, pharmaceuticals, oil or lubricants, cellulose, modified cellulose, regenerated cellulose, rayon, polymers of plastic materials, rubbers, ceramics, glass, silica, concrete, masonry or minerals.

14. A process as claimed in claim 12, wherein the polymers of plastic materials are vinyl polymers, acrylic polymers or polyesters.

15. A process as claimed in claim 13, wherein the polymers of plastic materials are vinyl polymers, acrylic polymers or polyesters.

16. A process as claimed in claim 10, wherein the matter is in the form of airconditioner filters, aprons, bags for laundry, bandages, tiles or grout, bricks, carpets, catheters or other related hospital instruments made from plastic or glass, clothing, food wraps, concrete, cottonballs or cotton tips, diapers, drapes, disposable cardboard or plastic food boxes, face masks, bed covers, inners of shoes, ironing board covers, nursing pads, paint, paper plates and cups, water reservoirs or swimming pool or water-treatment chemicals, rubbish bins, sanitary napkins or feminine hygiene tampons, shelving paper, shower curtains, teatowels, telephones, tents, tissues, handkerchiefs, toilet paper, toothbrushes, towels, wall paper, window awnings or other like structures made from canvas or plastic, wipes, mops, sponges, wood or wood-impregnants.

17. A process as claimed in claim 11, wherein the matter is in the form of airconditioner filters, aprons, bags for laundry, bandages, tiles or grout, bricks, carpets, catheters or other related hospital instruments made from plastic or glass, clothing, food wraps, concrete, cottonballs or cotton tips, diapers, drapes, disposable cardboard or plastic food boxes, face masks, bed covers, inners of shoes, ironing board covers, nursing pads, paint, paper plates and cups, water reservoirs or swimming pool or water-treatment chemicals, rubbish bins, sanitary napkins or feminine hygiene tampons, shelving paper, shower curtains, teatowels, telephones, tents, tissues, handkerchiefs, toilet paper, toothbrushes, towels, wall paper, window awnings or other like structures made from canvas or plastic, wipes, mops, sponges, wood or wood-impregnants.

18. A process for rendering a substrate biocidal or biostatic, which comprises polymerizing acrolein alone or with comonomers in the presence of the substrate material to chemically bind to the substrate, or to incorporate within the substrate, a biocidally or biostatically effective amount of an acrolein polymer or copolymer having at least the repeating polymeric unit

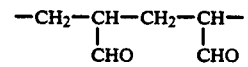

or the hydrated diol form thereof, the hemiacetal or acetal form thereof from condensation of the diol form with the aldehyde form, the tetrahydropyran or fused tetrahydropyran form thereof from self-condensation of the diol form, the aldol-Michael self-condensation form thereof or mixtures thereof.

19. An article of manufacture according to claim 1 wherein the substrate is water or a water-containing composition.

20. A process as claimed in claim 10, which comprises polymerizing acrolein, a copolymer or derivative thereof in the presence of a polymerization inducing agent, an ionic catalyst, gamma radiation, a free radical catalyst, ultraviolet radiation, electron beam radiation or a combination thereof.

21. A process as claimed in claim 18, which comprises polymerizing acrolein, a (co)polymer or a derivative thereof in the presence of a polymerization inducing agent, an ionic catalyst, gamma radiation, a free radical catalyst, ultraviolet radiation, electron beam radiation or a combination thereof.

22. A method of inhibiting microbial growth on a substrate comprising:
applying a biostatic or biocidal agent to the substrate sufficient to inhibit microbial growth in or on the substrate, wherein the biostatic or biocidal agent is a polymer or copolymer having a repeating polymeric unit

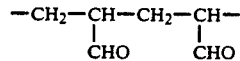

or the hydrated diol form thereof, the hemiacetal or acetal form thereof from condensation of the diol form with aldehyde form, the tetrahydropyran or fused tetrahydropyran form thereof from self-condensation of the diol form, the aldol-Michael self-condensation form thereof or mixtures thereof.

23. A method according to claim 22, wherein the step of applying a biostatic or biocidal agent to a substrate comprises polymerizing acrolein or a copolymer or derivative thereof in the presence of the substrate.

24. A process as claimed in claim 22, which comprises polymerizing acrolein, a copolymer or derivative thereof in the presence of a polymerization inducing agent, an anionic catalyst, gamma radiation, a free radical catalyst, ultraviolet radiation, electron beam radiation, or a combination thereof.

25. A process according to claim 22, wherein the substrate is selected from the group consisting of cellulose, modified cellulose, regenerated cellulose, rayon, polymers of plastic materials, rubbers, ceramics, glass, silicon, concrete, masonry, minerals and earths.

26. A process according to claim 22, wherein the substrate is selected from the group consisting of food, cosmetics, toiletries, oil, lubricants and water.

27. A process according to claim 22, wherein the substrate is selected from the group consisting of air conditioner filters, aprons, bags for laundry, bandages, tiles or grout, bricks, carpets, catheters, clothing, food wraps, concrete, cotton balls or cotton tips, diapers, drapes, disposable cardboard or plastic food boxes, face masks, bed covers, inners of shoes, ironing board covers, nursing pads, paint, paper plates, paper cups, water reservoirs, swimming pools, water treatment chemicals, rubbish bins, sanitary napkins, feminine hygiene tampons, shelving paper, shower curtains, tea towels, telephones, tents, tissues, handkerchiefs, toilet paper, toothbrushes, towels, wallpaper, window awnings or other like structures made from canvas or plastic, wipes, mops, sponges, and wood or wood impregnate.

* * * * *